United States Patent
Rowe et al.

(10) Patent No.: US 10,605,070 B2
(45) Date of Patent: Mar. 31, 2020

(54) DETERMINING THE CURRENT STATE OF CEMENT IN A WELLBORE

(71) Applicant: Halliburton Energy Services, Inc., Houston, TX (US)

(72) Inventors: Mathew Dennis Rowe, Lafayette, LA (US); Jon Troy Gosney, Bellville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 93 days.

(21) Appl. No.: 15/567,242

(22) PCT Filed: May 19, 2015

(86) PCT No.: PCT/US2015/031540
§ 371 (c)(1),
(2) Date: Oct. 17, 2017

(87) PCT Pub. No.: WO2016/186653
PCT Pub. Date: Nov. 24, 2016

(65) Prior Publication Data
US 2018/0135404 A1    May 17, 2018

(51) Int. Cl.
*E21B 47/00*   (2012.01)
*G01N 33/00*   (2006.01)
(Continued)

(52) U.S. Cl.
CPC ..... *E21B 47/0005* (2013.01); *G01N 33/0063* (2013.01); *G01N 33/383* (2013.01); *G08B 21/182* (2013.01); *E21B 33/14* (2013.01)

(58) Field of Classification Search
CPC ...................................................... E21B 47/00
See application file for complete search history.

(56) References Cited

U.S. PATENT DOCUMENTS

| | | |
|---|---|---|
| 4,769,601 A | 9/1988 | Herrick et al. |
| 6,053,245 A | 4/2000 | Haberman et al. |

(Continued)

FOREIGN PATENT DOCUMENTS

| | | |
|---|---|---|
| EP | 1335103 | 8/2003 |
| WO | 2014116251 | 7/2014 |
| WO | 2014171976 | 10/2014 |

OTHER PUBLICATIONS

Dr. HJH Brouwers, "Chemical Reactions in Hydrated Ordinary Portland Cement Based on the Work by Powers and Brownyard", 2003, 14 pages.

(Continued)

*Primary Examiner* — William D Hutton, Jr.
*Assistant Examiner* — Avi T Skaist
(74) *Attorney, Agent, or Firm* — Kilpatrick Townsend & Stockton LLP

(57) ABSTRACT

Systems and methods are provided for determining a cure state of cement in a wellbore. A drill device can be used to drill cement in a wellbore. Contact between the drill device and the cement can cause friction or heat, which can produce a gas. A gas detector can be positioned near a wellbore for detecting an amount of gas and a type of gas produced by contact between the drill device and the cement in the wellbore. The cure state of cement in the wellbore can be determined based on the amount of gas and the type of gas detected.

20 Claims, 7 Drawing Sheets

(51) Int. Cl.
*G01N 33/38* (2006.01)
*G08B 21/18* (2006.01)
*E21B 33/14* (2006.01)

(56) References Cited

U.S. PATENT DOCUMENTS

| | | | |
|---|---|---|---|
| 6,675,895 | B1 | 1/2004 | Vaeth et al. |
| 6,858,566 | B1 | 2/2005 | Reddy et al. |
| 7,124,030 | B2 | 10/2006 | Ellis et al. |
| 8,157,008 | B2 | 4/2012 | Lilley et al. |
| 8,636,063 | B2 * | 1/2014 | Ravi ............ E21B 33/14 166/253.1 |
| 8,776,609 | B2 | 7/2014 | Dria et al. |
| 8,881,843 | B2 | 11/2014 | Hannegan et al. |
| 2005/0241382 | A1 | 11/2005 | Coenen |
| 2007/0169540 | A1 | 7/2007 | Sterner et al. |
| 2008/0135236 | A1 | 6/2008 | Schoell et al. |
| 2009/0044617 | A1 | 2/2009 | Difoggio |
| 2011/0192592 | A1 | 8/2011 | Roddy et al. |
| 2011/0199228 | A1 * | 8/2011 | Roddy ............ E21B 33/13 340/856.4 |
| 2012/0229287 | A1 | 9/2012 | Schuetzle et al. |
| 2013/0002268 | A1 | 1/2013 | Kumar et al. |
| 2013/0031964 | A1 | 2/2013 | Tunheim et al. |
| 2013/0098604 | A1 | 4/2013 | Ramakrishnan et al. |
| 2013/0118752 | A1 | 5/2013 | Hannegan et al. |
| 2014/0076549 | A1 | 3/2014 | Pelletier et al. |
| 2015/0003203 | A1 | 1/2015 | Froelich |

OTHER PUBLICATIONS

Halliburton Energy Services, Inc , "Innovative Cement Enhancements", at least as early as 2008, 6 pages.

International Patent Application No. PCT/US2015/031540 , "International Search Report and Written Opinion", dated Mar. 10, 2016, 16 pages.

Zhang et al., "Early Hydration and Setting of Oil Well Cement", Abstract, at least as early as Jan. 29, 2008, 1 page.

\* cited by examiner

DETERMINING THE CURRENT STATE OF CEMENT IN A WELLBORE

TECHNICAL FIELD

The present disclosure relates generally to wellbore drilling. More specifically, but not by way of limitation, this disclosure relates to determining an extent of curing of cement in the wellbore based on a type of gas and an amount of gas produced during drilling operations.

BACKGROUND

A well system (e.g., oil or gas wells for extracting fluids from a subterranean formation) can include a drilling rig for drilling in a wellbore, along with other components or equipment. During drilling operations, a casing is run into the wellbore and set into place by injecting cement between the casing, or a liner, and the wellbore. It may be challenging to determine the extent of curing of the cement in the wellbore before continuing with other drilling operations.

DETAILED DESCRIPTION

Figure 1:
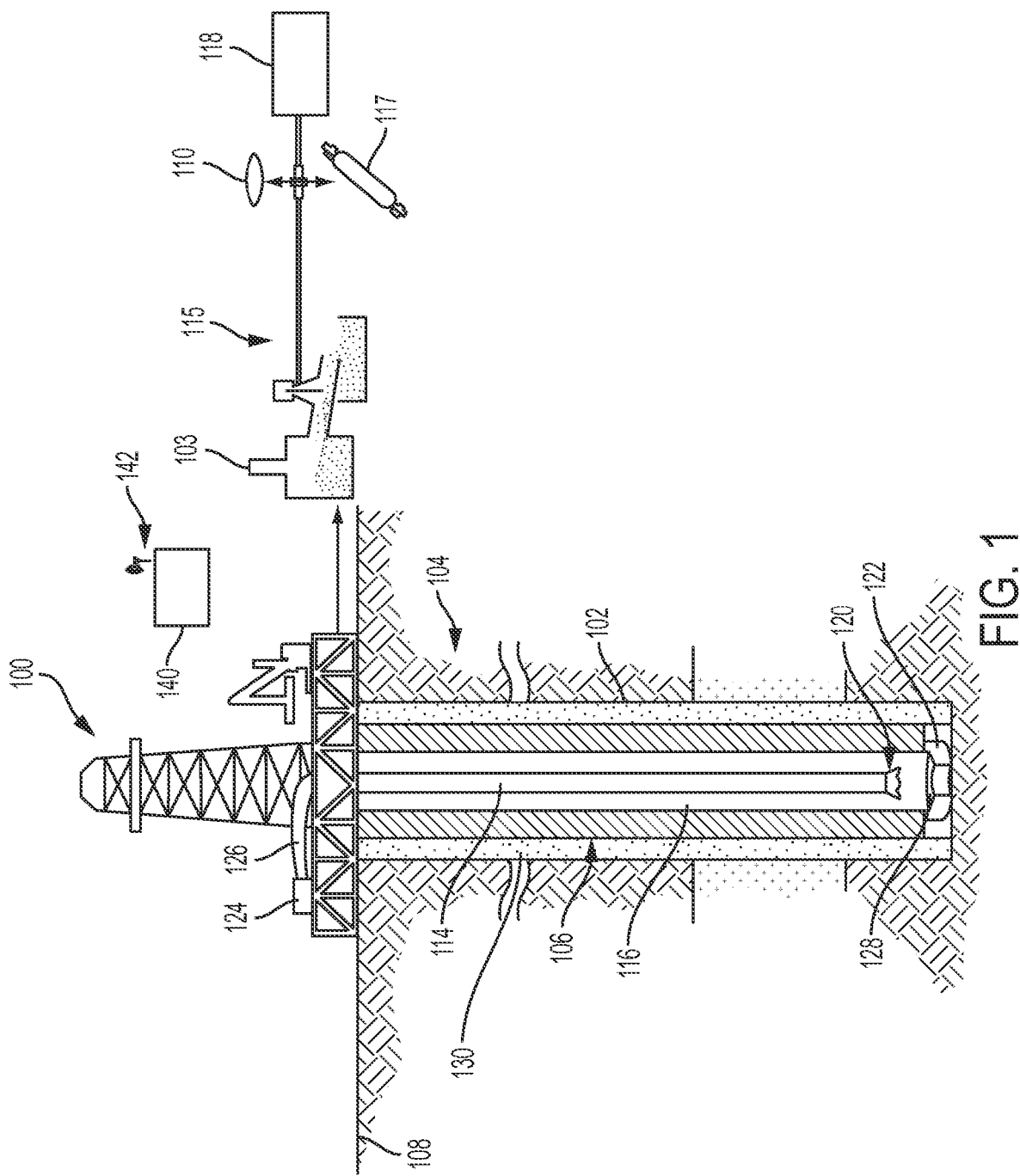
FIG. 1 is a schematic diagram showing a drilling rig on a wellbore, along with a casing string.

Certain aspects and features of the present disclosure are directed to determining an extent of curing (e.g., an extent of aging) of cement in a wellbore based on gas produced during drilling operations. During drilling operations, a drilling fluid circulation system or mud system circulates drilling fluid or mud through the wellbore via a drill string. When a proper depth within the wellbore has been reached per a well plan, the drill string can be removed from the wellbore and the drilling fluid may remain in the wellbore. A casing can then be run into the wellbore. The casing can be coupled to a casing shoe or guide shoe. The casing shoe can guide the casing through the wellbore, as the casing is run into the wellbore. The casing can be set in place in the wellbore by pumping cement down the casing and back up an annulus (e.g., an annulus created between the casing and the wellbore). Various techniques may be employed to prevent contamination of the cement with the drilling fluid. For example, a top plug and a bottom plug may be used to prevent such contamination. The bottom plug can be inserted at a wellhead of the wellbore. Cement can be used to push the bottom plug down the casing toward the bottom of the casing, which may allow the cement to flow back up the annulus. Allowing the cement to flow back up the annulus may bond the casing to the wellbore or bond the casing to a formation through which the wellbore extends. A top plug may be put into place when a sufficient amount of cement has been pumped into the wellbore. Drilling fluid may be used to push the top plug toward the bottom plug, which may increase the pump pressure and indicate that the cement pumping operation is complete.

After the cement is cured, other drilling operations may begin. For example, the drill string can be lowered toward the bottom of the cemented wellbore. A drill bit can be used to drill out cement in the wellbore. As an example, the drill bit can be used to drill out cement in the casing shoe after the casing is set in the wellbore. Drilling out the cement in the casing shoe can allow further drilling operations. While drilling out cement in wellbore, contact between the drill bit and the cement can create friction or heat, which can produce a gas. The extent of curing of cement in the wellbore (e.g., cement in the casing shoe or cement between the casing and the wellbore) can be determined based on the amount of gas and the type of gas produced. The extent of curing of cement in the wellbore can be determined based on a concentration of carbon dioxide ($CO_2$), hydrogen ($H_2$), oxygen ($O_2$), or water ($H_2O$) in the gas produced. For example, the concentration of $CO_2$ in the gas can be higher than the concentration of water $H_2O$ in the gas if the cement is cured. The gas produced can also include a higher concentration of $H_2$ than $CO_2$ if the cement is cured. In other examples, if the cement is not cured, the concentration of $H_2O$ in the gas can be higher than the concentration of $CO_2$ in the gas. The gas produced can also include a higher concentration of $CO_2$ than $H_2$ if the cement is not cured. Efficiently determining the extent of curing of cement in the wellbore can lead to effective planning of subsequent drilling operations.

For example, during drilling operations, a drill bit can be used to drill cement in a casing shoe that is attached to a casing in a wellbore. Contact between the drill bit and cement can produce a gas. Together, the cement along with the gas may form a cement slurry. In some examples, the cement slurry may include any fluid that includes the cement (e.g., drilling fluid that includes hydraulic cement) or any other type of material (e.g., polymer) used in place of, or in addition to a hydraulic cement. In other examples, the cement slurry may include foamed cement. The cement slurry may flow toward a surface of the wellbore along a flow path provided by the casing or along an annulus between the wellbore and the casing. A gas detector device (e.g., a mass spectrometer, a purge trap device, a catalytic gas detector, an infrared gas detector, an electrochemical gas detector, or an integrated computational element) can be positioned at the surface of the wellbore for detecting the gas in the cement slurry. In some examples the gas detector device can detect an amount of gas and a type of gas in the cement slurry. The gas detector can transmit this data to a computing device. In other examples, the gas detector device can detect a concentration level of an amount of gas and a type of gas in the cement slurry. The gas detector device can transmit this data to the computing device. For example, the gas detector device can detect a concentration of $CO_2$, $H_2$, $O_2$, or $H_2O$ in the amount of gas and the type of gas in the cement slurry and transmit this data to the computing device. The computing device can determine an extent of curing of cement in the wellbore based on data received from the gas detector device. In some examples, the computing device can output an alarm in response to determining that the extent of curing of cement in the wellbore is below a threshold.

In some examples, other data can be used along with data received from the gas detector device to determine the extent of curing of cement in the wellbore. For example, the computing device can determine the extent of curing of cement based on the amount of gas and the type of gas detected at the surface of the wellbore by the gas detector device, and a type of cement being drilled in the casing shoe. In another example, the computing device can determine the extent of curing of cement based on the amount of gas and the type of gas detected, and a type of drill bit (e.g., a rock drill bit or a polycrystalline diamond compact drill bit) used to drill cement in the casing shoe. In still another example, the computing device can determine the extent of curing of cement based on the amount of gas and the type of gas detected, and an amount of gas and a type of gas entering and exiting the wellbore (e.g., based on a mass balance equation).

The computing device may also generate and output data for determining the extent of curing of cement in the wellbore. For example, the computing device may generate and output data representing an amount and a type of gas detected at the surface of the wellbore by the gas detector device. In other examples, the data may represent a concentration level of an amount of gas and a type of gas detected at the surface of the wellbore by the gas detector device for determining the extent of curing of cement in the wellbore.

Determining the extent of curing of cement in a wellbore in real-time can enhance drilling operations on a wellbore. For example, efficiently determining the extent of curing of cement in the wellbore can lead to effective planning for subsequent drilling operations, such as helping to determine whether to: (i) stop drilling operations and wait for an increase in pressure, (ii) take a formation integrity test (FIT), (iii) perform a leak-off test, (iv) add more cement into the wellbore, (vi) perform a hook-load test on the casing, or (vii) remove the casing from the wellbore and run the casing back into the wellbore. Efficiently determining the extent of curing of cement in the wellbore may also help prevent well control issues.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

FIG. 1 is a schematic diagram showing a drilling rig 100 on a wellbore 102, along with a casing string 106.

In this example, the drilling rig 100 is depicted for a well system (e.g., an oil or gas well for extracting fluids from a hydrocarbon bearing subterranean formation 104). The drilling rig 100 may be used to create a borehole or wellbore 102 that extends through various earth strata (e.g., the subterranean formation 104).

The well system can include a casing or casing string 106 that extends from a surface 108 to the subterranean formation 104. The casing string 106 can be run into the wellbore 102 to provide a conduit through which fluids, such as drilling fluids, can travel from the surface 108 to the wellbore 102 or from the wellbore 102 to the surface 108. The casing string 106 can be coupled to a casing shoe 122. The casing shoe 122 can be used to guide the casing string 106 into the wellbore 102. For example, the casing shoe 122 can be used to guide the casing string 106 past cuttings and other debris in the wellbore 102 that may prevent the casing string 106 from being positioned within the wellbore 102. In some examples, the casing shoe 122 may be used to protect the casing string 106 from damage from the impact of landing the casing string 106 on the bottom of the wellbore 102. The casing shoe 122 can also include a cemented interior 128. In some examples, a pump 124 can pump cement 126 into the casing shoe 122 to form the cemented interior 128.

The casing string 106 can be positioned within the wellbore 102 to isolate formations that are adjacent to the wellbore 102. The casing string 106 can be coupled to the walls of the wellbore 102 via cement when the casing string 106 is positioned within the wellbore 102. For example, the pump 124 can inject cement 126 between the casing string 106 and the walls of the wellbore 102 for coupling the casing string 106 to the wellbore 102. A cement sheath 130 can be positioned (e.g., formed) between the casing string 106 and the walls of the wellbore 102 for coupling the casing string 106 to the wellbore 102. The type of cement used to form the cement sheath 130 or the type of cement injected between the casing string 106 and the wellbore 102 can include standard cement, foam cement, polymer cement, or the like.

The drilling rig 100 can also include at least one drill string 114. The drill string 114 can be coupled to a coiled tubing that can be wound around a reel and deployed into the wellbore 102. In other examples, the drill string 114, along with any components of the drill string 114, can be coupled to a drill pipe and rotated by a top drive or rotary table on the drilling rig 100.

The drill string 114 can include a milling device or a drill bit 120. The drill bit 120 may be any device for cutting or removing particles from within the wellbore 102. During drilling operations, drilling fluid may be pumped through the drill string 114. Pumping drilling fluid through the drill string 114 may allow the drill bit 120 to drill or cut through geological formation (e.g., the formation 104) of the wellbore 102. In some examples, the drilling fluid may exit the drill bit 120 and return to the surface 108 via an annulus 116 positioned between the drill string 114 and a wall of the casing 106. In other examples, drilling fluid may be used to maintain sufficient bottom hole pressure. Maintaining sufficient bottom hole pressure may prevent the wellbore 102 from collapsing in a newly drilled section of the wellbore 102. The drill bit 120 can also drill cement within the wellbore 102. For example, the drill bit 120 can be used to drill the cemented interior 128 of the casing shoe 122 after the casing string 106 is positioned within the wellbore 102. Drilling the cemented interior 128 can allow subsequent drilling operations. Contact between the drill bit 120 and cement in the wellbore 102 (e.g., the cemented interior 128) can produce a gas. The type of gas produced may depend on the extent of curing of the cement in the wellbore 102. The gas, cement, and other particles from within the wellbore that are cut by the drill bit 120, can be contained within the drilling fluid to form a cement slurry. The cement slurry can flow along the annulus 116 back to the surface 108.

At the surface 108, the gas and the cement within the cement slurry may be analyzed. For example, the well system may include a mud tank 103. The mud tank 103 may be used to receive or collect the cement slurry from within the wellbore 102. The mud tank 103 can be coupled to a suction tube 115 for providing the cement slurry to the suction tube 115. The suction tube 115 may be used to extract a fluid from the cement slurry. A degasser may be coupled to the suction tube 115. The degasser may include a gas sampling device 110 or a cylinder 117. In some examples, an inert gas (e.g., nitrogen or air) can be injected into the cement slurry. Injecting the inert gas into the cement slurry may pressurize the cement slurry. In other examples, injecting the inert gas into the cement slurry may allow the cement slurry to flow into the degasser. The degasser may be used to separate the gas from the drilling fluid in the cement slurry. In some examples, the drilling fluid can exit the degasser via an outlet and be processed for use in further drilling operations. In other examples, the mud tank 103, the suction tube 115, the gas sampling device 110, or the cylinder 117 is not included in the well system.

The well system can also include a gas detector 118. In some examples, the gas detector 118 can be coupled to the degasser for receiving gas from the degasser. In other examples when a degasser is not included in the well system, the gas detector 118 can be positioned closer to the surface 108 of the wellbore 102 so that the gas from the wellbore 102 may flow directly into the gas detector 118. The gas detector 118 can be positioned proximate to the wellbore 102. For example, the gas detector 118 can be positioned at the surface 108 of the wellbore. The gas detector 118 can detect gas at the surface 108 of the wellbore. For example, the gas detector 118 can detect an amount of gas and a type of gas produced from within the wellbore. In another example, the gas detector 118 can detect an amount of gas and a type of gas entering the wellbore and an amount of gas and a type of gas exiting the wellbore. Positioning the gas detector 118 proximate to the wellbore 102 can allow the gas detector 118 to efficiently detect a gas produced from within the wellbore (e.g., gas produced by contact between the drill bit 120 and cement in the wellbore 102).

In some examples, the gas detector 118 is not included in the well system. A sample of the cement slurry may be collected from the wellbore 102, including without limitation, through manual collection (e.g., manual labor) or through automated collection (e.g., by an apparatus, device, machine, or the like). The sample may be transported to a location (e.g., to an onsite or offsite laboratory) for analyzing the sample. In some examples, the sample may be analyzed for determining an extent of curing of cement in the wellbore 102.

The well system can also include, among other things, a computing device 140. The computing device 140 can be positioned at the surface 108 of the wellbore 102, below ground, or offsite. The computing device 140 can include a communication device 142 for transmitting and receiving data. The communication device 142 can represent one or more of any components that facilitates a network connection. The computing device 140 can be communicatively coupled to the gas detector 118 via a wired or wireless link. The computing device 140 can also transmit data to a remote location (e.g., an offsite laboratory or another computing device) via the communication device 142. In some examples, the computing device 140 can also receive data from the remote location via the communication device 142.

The computing device 140 may be used to determine an extent of curing of cement in the wellbore. Determining the extent of curing of cement in the wellbore (e.g., cement in the cemented interior 128 or cement between the casing string 106 and the wellbore 102) can lead to effective planning for the subsequent drilling operations and can help prevent well control issues.

Figure 2:
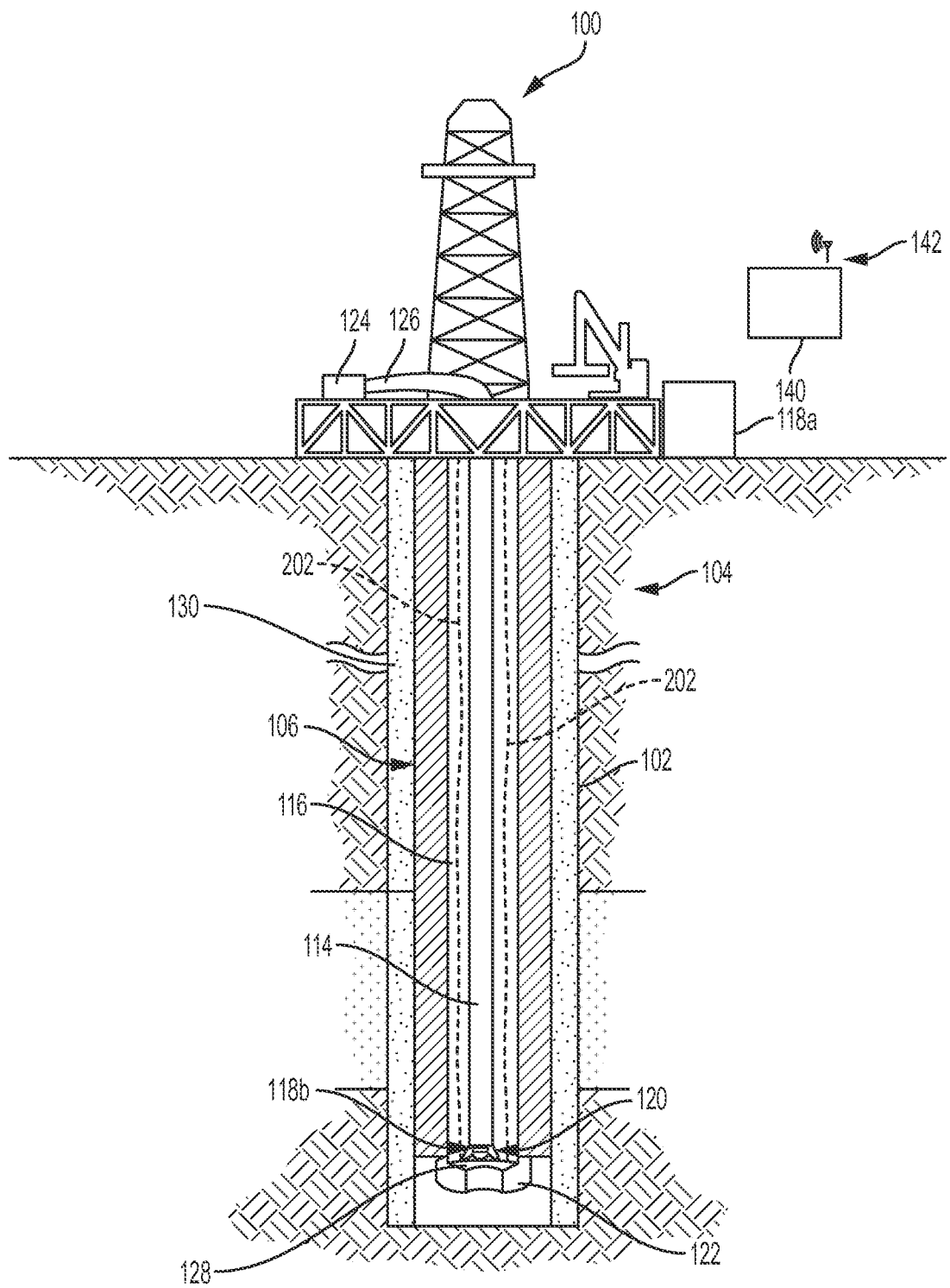
FIG. 2 is a schematic diagram showing the drilling rig of FIG. 1, along with gas in a fluid traveling from within the wellbore to the surface of the wellbore.

In some examples, the gas detector 118 along with the computing device 140 can be used to determine the extent of curing of cement in the wellbore based on gas from within the wellbore 102. FIG. 2 is a schematic diagram of the drilling rig of FIG. 1, along with gas 202 in a fluid traveling from within the wellbore 102 to the surface 108 of the wellbore 102.

In this example, the drill bit 120 can drill cement within the wellbore 102. For example, the drill bit 120 can drill the cemented interior 128 of the casing shoe 122. Contact between the drill bit 120 and cement in the wellbore (e.g., the cemented interior 128) can create friction or heat, which can produce gas 202. The gas 202 can include any amount of gas or type of gas that can be produced by friction or heat. The gas 202 may also include drilling fluid gas. Drilling fluid gas may include nitrogen that can be injected into drilling fluid for underbalanced drilling operations. In other examples, the gas 202 may include any gas from the formation 104. The gas 202, along with cement and drilling fluid from the wellbore may flow to the surface via annulus 116.

In some examples, more than one gas detector may be used to detect gas produced by contact between the drill bit 120 and cement within the wellbore. For example, gas detectors 118a-b can be used to detect gas 202 produced from within the wellbore. The gas detectors 118a-b can be of the same type or can be different. The gas detectors 118a-b can be positioned at the surface of the wellbore, on the casing 106, on or within the drill bit 120, or elsewhere in the well system for detecting the gas 202. The gas detectors 118a-b can detect gas 202 produced by contact between the drill bit 120 and the cement in the wellbore. For example, the gas detectors 118a-b can detect gas 202 produced by contact between the drill bit 120 and the cemented interior 128. The gas detectors 118a-b can detect an amount of gas and a type of gas in gas 202. In some examples, the gas detectors 118a-b can detect a concentration level of an amount of gas and a type of gas in the gas 202. The gas detector 118a-b can also detect a concentration of $CO_2$, $H_2$, $O_2$, or $H_2O$ in the amount of gas and the type of gas 202 produced by contact between the drill bit 120 and cement in the wellbore.

In another example, the gas detectors 118a-b can detect an amount of gas and a type of gas entering the wellbore 102 and an amount of gas and a type of gas exiting the wellbore 102. For example the gas detector 118a can be positioned proximate to the surface 108. The gas detector 118a can detect an amount of gas and a type of gas entering the wellbore 102. The gas detector 118b can be positioned within the wellbore 102. The gas detector 118b can detect an amount of gas and a type produced by contact between the drill bit 120 and the cemented interior 128. The gas detectors 118a-b can also detect an amount of gas and a type of gas exiting the wellbore.

In some examples, the gas detector 118b shown FIG. 2 can be positioned such that the gas detector 118 is partially within or fully within the wellbore 102. For example, the gas detector 118b can be positioned on an outer housing of the drill bit 120. In other examples, the gas detector 118b can be positioned within the outer housing of the drill bit 120. The gas detector 118b may transmit data (e.g., to the computing device 140) via a wired drill pipe, a wired coil tubing, or by using other telemetry schemes (e.g., acoustic telemetry, electromagnetic telemetry, mud pulse telemetry, or any combination thereof) if the gas detector 118b is positioned partially within or fully within the wellbore. Positioning the gas detector 118b partially within or fully within the wellbore can allow the gas detector 118b to more accurately and efficiently detect gas produced by contact between the drill bit 120 and cement in the wellbore. Accurately detecting gas produced can allow a more accurate analysis of an extent of curing of cement in the wellbore.

In still another example, any of the gas detectors 118a-b and a computing device can be integrated into a single structure. For example, a gas detector (e.g., the gas detectors 118a-b) and a computing device (e.g., the computing device 140) can be within a single housing (e.g., a logging unit). The computing device may be communicatively coupled to a display device of the logging unit for outputting data. The computing device can include a communication device (e.g., the communication device 142) for transmitting and receiving data. The computing device may transmit data to a remote location (e.g., to a drilling or well operator or another computing device).

Figure 3:
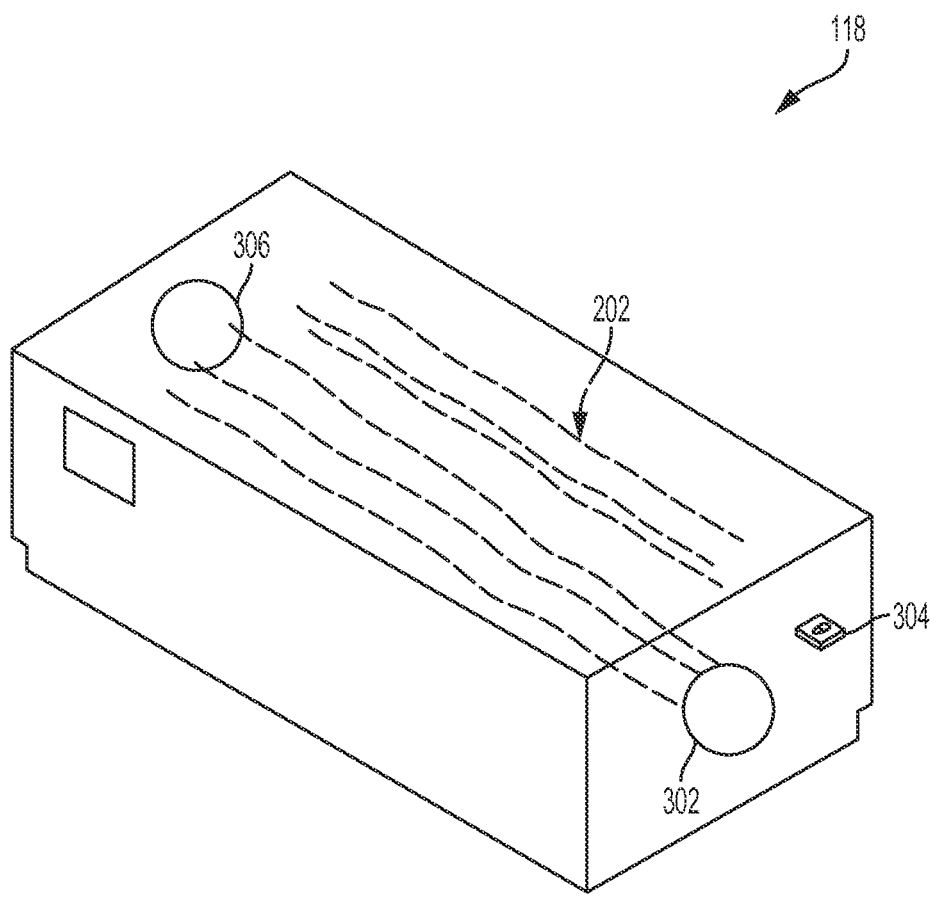
FIG. 3 is a perspective view of an example of a gas detector and gas from a wellbore.

FIG. 3 is a perspective view of an example of a gas detector 118 and gas 202 from a wellbore. The gas detector 118 is shown via a transparent view and may be any type of device operable in a well system for measuring an amount of gas or detecting a type of gas. For example, the gas detector 118 can be a mass spectrometer, a purge trap device, a catalytic gas detector, an infrared gas detector, an electromechanical gas detector, or an integrated computational element for detecting an amount of gas and a type of gas. Examples of an integrated computational element and further details of an integrated computational element are described in U.S. Patent Pub. No. 2013/0031964 entitled "Systems and Methods for Monitory the Quality of a Fluid." The gas detector 118 can have a gas input 302. The gas input 302 can allow gas to flow into the gas detector 118. The gas detector 118 can also have a gas output 306. The gas output 306 can allow gas to exit the gas detector 118.

The gas detector 118 can detect an amount of gas and a type of gas produced from within a wellbore. For example, the gas detector 118 can detect an amount and a type of gas 202 from the wellbore by collecting gas 202 at the surface of the wellbore, via the gas input 302. In some examples, the gas detector 118 may detect an amount of gas or a type of gas by measuring a mass-to-charge ratio of molecules in gas 202 from the wellbore.

In another example, the gas detector 118 can detect a concentration level of an amount of gas and a type of gas at the surface of the wellbore. For example, the gas detector 118 can detect a concentration of $CO_2$, $H_2$, $O_2$, or $H_2O$ in the gas 202. In some examples, the gas detector 118 can include a gas sensor 304 for detecting the presence of an amount of gas and a type of gas prior to the gas entering the gas detector 118 via the gas input 302. In still another example, the gas detector 118 can detect an amount of gas and a type of gas entering the wellbore and an amount of gas and a type of gas exiting the wellbore. The gas detector 118 can also be communicatively coupled to a computing device (e.g., the computing device 140) via a wired or a wireless link. The gas detector 118 can transmit data about gas detected at the surface of the wellbore to the computing device.

Figure 4:
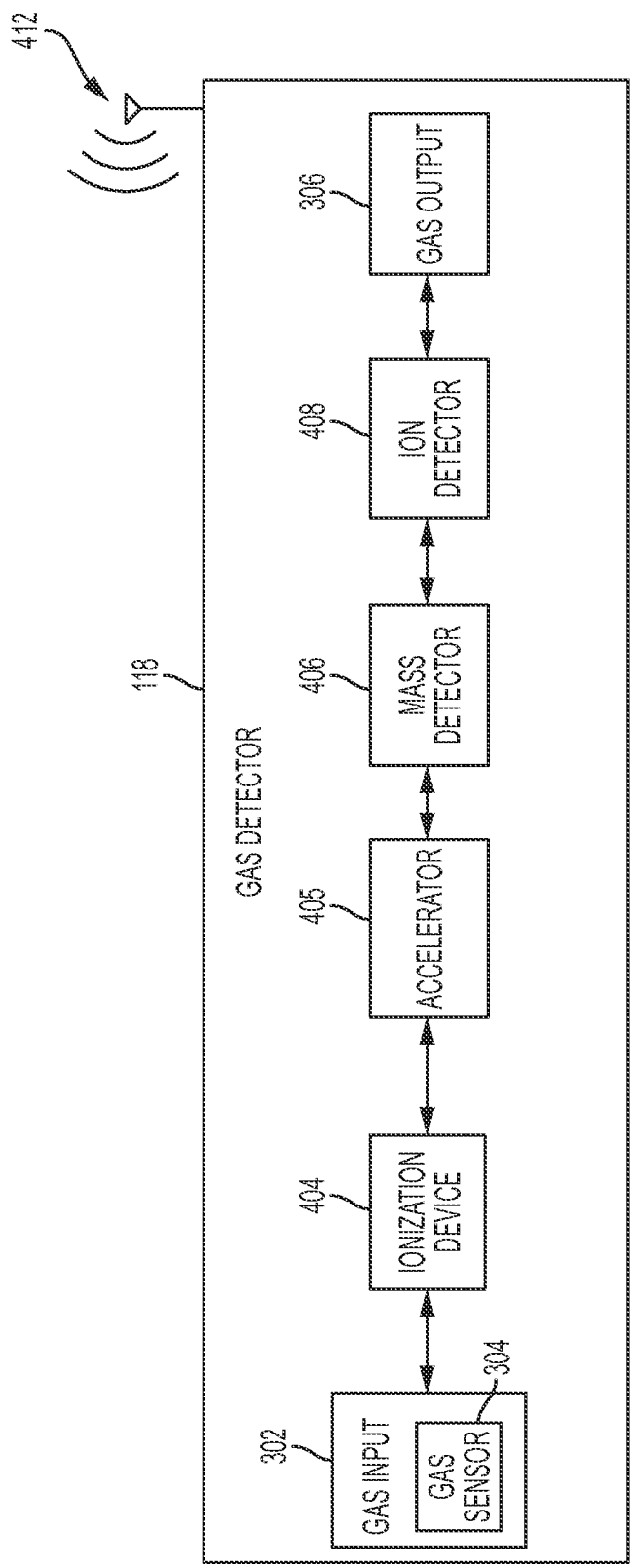
FIG. 4 is a block diagram of an example of the gas detector of FIG. 3.

In some examples, the gas detector 118 can include additional components for detecting an amount of gas and a type of gas. For example, FIG. 4 is a block diagram of an example of the gas detector 118 of FIG. 3. The gas detector 118 can include the gas input 302, a gas sensor 304 and the gas output 306.

The gas input 302 may allow gas to enter the gas detector 118. For example, gas may flow from within a wellbore (e.g., the wellbore 102) to a surface of the wellbore (e.g., the surface 108) and into the gas input 302. The gas sensor 304 can detect the presence of an amount of gas and a type of gas prior to the gas entering the gas input 302. In this example, the gas sensor 304 can be coupled to the gas input 302. In other examples, the gas sensor 304 may be coupled to any component of the gas detector 118. In still another example, the gas sensor 304 may be in a separate housing. The gas output 306 may allow gas to exit the gas detector 118. For example, the gas may flow out of the gas detector 118 via the gas output 306 after the gas is detected by the gas detector 118.

In this example, the gas detector 118 can be a mass spectrometer. The gas detector 118 can include an ionization device 404, an accelerator 405, a mass detector 406 and an ion detector 408. The ionization device 404 can be any device for converting a chemical compound into ions. The ionization device 404 can convert a chemical compound into ions by any ionization method, including, for example, protonation, cationization, deprotonation, etc. In some examples, gas from a wellbore (e.g., the gas 202) can flow into the gas detector 118 via the gas input 302. The ionization device 404 can convert the gas within the gas detector 118 into ions as the gas enters the gas detector 118.

The accelerator 405 can be any device for propelling or accelerating ions. In some examples, the accelerator 405 can be coupled to the ionization device 404. The accelerator 405 may propel ions from the ionization device 404 into the mass detector 406. For example, the accelerator 405 may electrostatically propel ions from the ionization device 404 to the mass detector 406 using electric charges or fields.

The mass detector 406 can analyze ions produced by the ionization device 404. In some examples, the mass detector 406 can analyze ions by separating ions. The mass detector 406 can separate ions based on a charge to mass ratio of each ion. For example, the mass detector 406 can generate an electric or magnetic field. The electric or magnetic field can deflect ions propelled into the mass detector 406 by the accelerator 405. The amount of deflection of each ion can vary based on the mass of the ion and the charge of the ion. For example, an ion with a lower mass can be deflected more than an ion with a higher mass. As another example, an ion with a more positive charge can be deflected more than ion with a less positive charge. The mass detector 406 can separate the ions based on a charge to mass ratio of each ion.

The ion detector 408 can be any device for detecting charged particles (e.g., an electron multiplier). In some examples, the mass detector 406 may be coupled to the ion detector 408. The mass detector 406 may discharge ions into the ion detector 408 based on the charge to mass ratio of each ion. The ion detector 408 can detect each ion as the ions flow through the ion detector 408. For example, the ion detector 408 can detect each ion based on a current generated as the ion travels through the ion detector 408. The gas detector 118 can transmit data about each ion to a computing device (e.g., the computing device 140) as the ion detector 408 detects each ion. In some examples, the gas detector 118 can transmit data about an amount and types of ions detected by the ion detector 408 to the computing device for determining an amount of gas and a type of gas detected by the gas detector 118.

The gas detector 118 can transmit and receive data from the computing device via a communication device 412. In some examples, the communication device 412 can represent one or more of any components that facilitate a network connection. In some examples, the communication device 412 may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 412 can be wired and can include interfaces such as Ethernet, USB, IEEE 1394, or a fiber optic interface.

Figure 5:
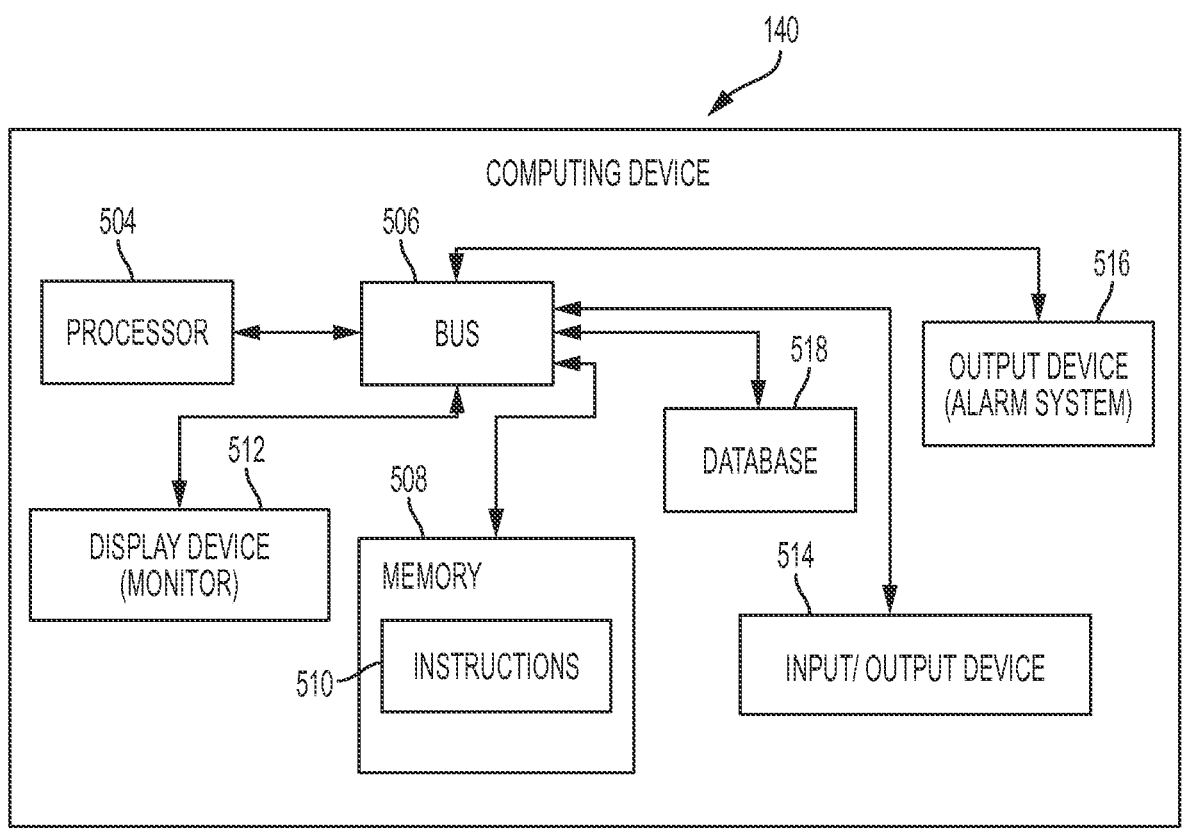
FIG. 5 is a block diagram of an example of a computing device for determining an extent of curing of cement in a wellbore.

FIG. 5 is a block diagram of an example of a computing device 140 for determining an extent of curing of cement in a wellbore. The computing device 140 can include a processor 504, a memory 508, and a bus 506. The processor 504 can execute one or more operations for operating the computing device 140. The processor 504 can execute instructions 510 stored in the memory 508 to perform the operations. Non-limiting examples of the processor 504 include a Field-Programmable Gate Array ("FPGA"), an application-specific integrated circuit ("ASIC"), a microprocessor, etc.

The processor 504 can be communicatively coupled to the memory 508 via the bus 506. The memory 508 may include any type of memory device that retains stored information when powered off. Non-limiting examples of the memory 508 include electrically erasable and programmable read-only memory ("EEPROM"), flash memory, or any other type of non-volatile memory. In some examples, at least some of the memory 508 can include a computer-readable medium from which the processor 504 can read the instructions 510. The computer-readable medium can include electronic, optical, magnetic, or other storage devices capable of providing the processor 504 with computer-readable instructions or other program code. Non-limiting examples of a computer readable-medium include (but are not limited to) magnetic disk(s), memory chip(s), ROM, random-access memory ("RAM"), an ASIC, a configured processor, optical storage, or any other medium from which a computer processor can read instructions. The instructions can include processor-specific instructions generated by a compiler or an interpreter from code written in any suitable computer-programming language, including, for example, C, C++, C #, etc.

In some examples, the computing device 140 can include input/output interface components (e.g., a display device 512, a communication device 514, and an alarm system 516). The computing device 140 can also include other input/output interface components such as a display, a keyboard, touch-sensitive surface, mouse and additional storage.

The computing device 140 can receive data from a gas detector via a communication device 514. The computing device can also receive data from a remote location via the communication device 514. In some examples, the communication device 514 can represent one or more of any components that facilitate a network connection. In some examples, the communication device 514 may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 514 can be wired and can include interfaces such as Ethernet, USB, IEEE 1394, a landline, or a fiber optic interface.

The processor 504 can include one processing device or multiple processing devices. The processor 504 can execute one or more operations for determining an extent of curing of cement in a wellbore. For example, the processor 504 can execute one or more operations for determining a cure state of cement in the wellbore based on data transmitted from a gas detector device (e.g., the gas detector 118). In another example, the processor 504 can execute one or more operations for generating and outputting data for determining a cure state of cement in the wellbore based on data transmitted from the gas detector device.

In some examples, the processor 504 can execute one or more operations for determining a cure state of cement in the wellbore based on data from the gas detector device and other data. The other data can be any data, including, for example, a type of cement in the wellbore, a type of drill device used to drill cement in the wellbore, an amount and type of gas entering and exiting the wellbore, etc. The memory 508 can include instructions for receiving the other data (e.g., from another computing device) or indicia of a user input (e.g., if the user programs the computing device 140 to include the other data).

In still another example, the processor 504 can execute one or more operations for causing the computing device 140 to transmit data to a remote location (e.g., an offsite laboratory) for determining a cure state of cement in the wellbore. In some examples, the data may be analyzed at the remote location (e.g., by an operator or by another computing device) for determining the cure state of cement in the wellbore. The processor 504 may execute one or more operations for causing the computing device 140 to receive other data from the remote location. The other data may represent the cure state of cement in the wellbore. In some examples, the computing device 140 may output an alarm (e.g., using the alarm system 516) based on the other data received from the remote location.

The processor 504 can also execute operations for recognizing a threshold of an extent of curing of cement in the wellbore. The computing device 140 can be communicatively coupled to the alarm system 516 via the bus 506. If the extent of curing of cement in the wellbore is below the threshold, the processor 504 can execute one or more operations for outputting an alarm, through the alarm system 516, in response to such conditions.

In some examples, the computing device 140 can also be communicatively coupled to a display device 512 via the bus 506. The display device 512 can display data that may correspond to data received by the computing device 140 from the gas detector device. The display device 512 may also display data that may correspond to data generated by executing an operation executed by the processor 504.

The computing device 140 can also be communicatively coupled to a database 518 via the bus 506. The database 518 can store data that may correspond to data received by the computing device 140 from the gas detector device. The database 518 may also store data that may correspond to data generated by an operation executed by the processor 504. In still another example, the database 518 may store data that may correspond to data received by the computing device 140 from a remote location (e.g., from a computing device positioned at the remote location) or indicia of user input (e.g., if a user programs the computing device to include data). In some examples, the processor 504 can execute one or more operations for determining subsequent drilling operations based on data in the database 518. For example, the processor 504 can execute one or more operations for comparing data in the database 518 for determining properties of subsequent fluids (e.g., drilling fluids) or subsequent cement to be injected into the wellbore based on the comparison. The data in the database 518 can include: (i) geological properties of a formation through which the wellbore extends (e.g., formation 104), (ii) a type of casing string in the wellbore (e.g., the casing string 106), (iii) drilling fluids in the wellbore, (iv) cure time of cement in the wellbore, (v) wellbore temperature, or other data.

Figure 6:
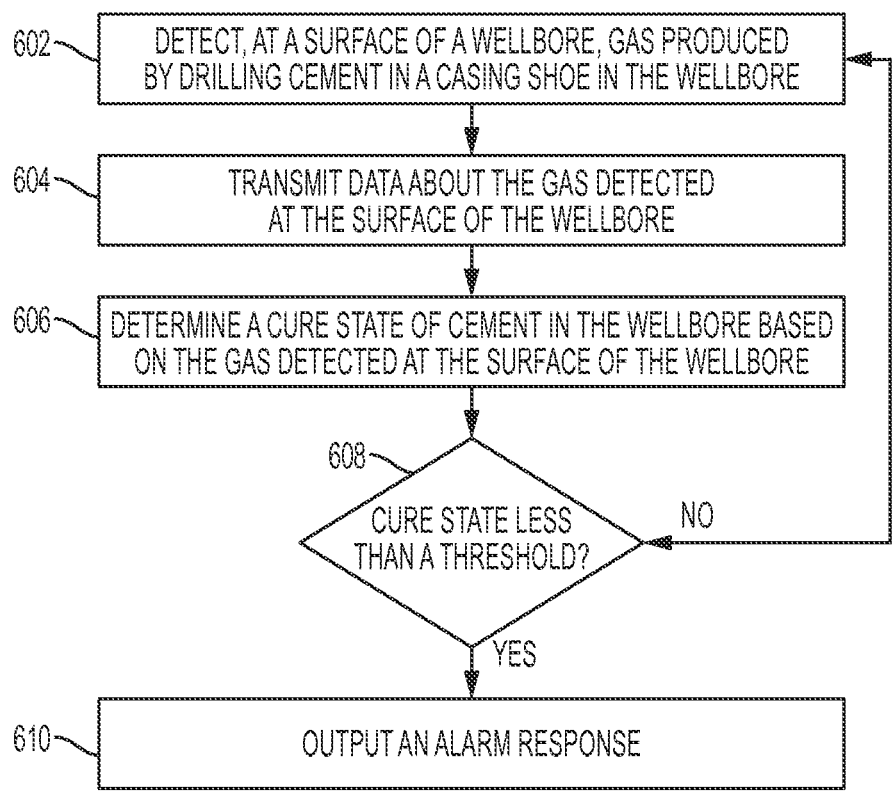
FIG. 6 is a flow chart depicting an example of a process for determining a cure state of cement in a wellbore.

FIG. 6 is a flow chart depicting an example of a process for determining a cure state of cement in a wellbore.

In block 602, gas produced by drilling cement in a casing shoe in a wellbore is detected at the surface of the wellbore by a gas detector device (e.g., the gas detector 118). In some examples, a drill device (e.g., the drill bit 120) can be used to drill cement (e.g., the cemented interior 128) in a casing shoe that is coupled to a casing string (e.g., the casing string 106). Contact between the drill device and cement in the casing shoe can create friction or heat, which can produce a gas (e.g., $CO_2$, $H_2$, $O2$, or $H_2O$). The gas can flow from within an annulus of the wellbore to a surface of the wellbore.

The gas detector device can detect the gas produced by drilling cement in the casing shoe. The gas detector device can include a mass spectrometer, a purge trap device, a catalytic gas detector, an infrared gas detector, an electrochemical gas detector, or an integrated computational element. The gas detector device can detect an amount of gas and a type of gas produced by drilling cement in the casing shoe. The gas detector device may detect a concentration level of the amount of gas and the type of gas produced by drilling cement in the casing shoe. The gas detector device may also detect a concentration of $CO_2$, $H_2$, $O_2$, or $H_2O$ in the amount of gas and the type of gas produced by drilling cement in the casing shoe.

In block 604, data about the gas detected at the surface of the wellbore is transmitted to a computing device (e.g., the computing device 140). In some examples, the gas detector device can transmit data to the computing device. The data may represent an amount and a type of gas detected at the surface of the wellbore. The gas detector device may transmit other data that represents a concentration level of the amount of gas and the type of gas detected at the surface of the wellbore. The data may also represent a concentration of $CO_2$, $H_2$, $O_2$, or $H_2O$ in the amount of gas and the type of gas detected at the surface of the wellbore. In some examples, the data my represent an amount of gas and a type of gas entering the wellbore and an amount of gas and a type of gas exiting the wellbore.

Figure 7:
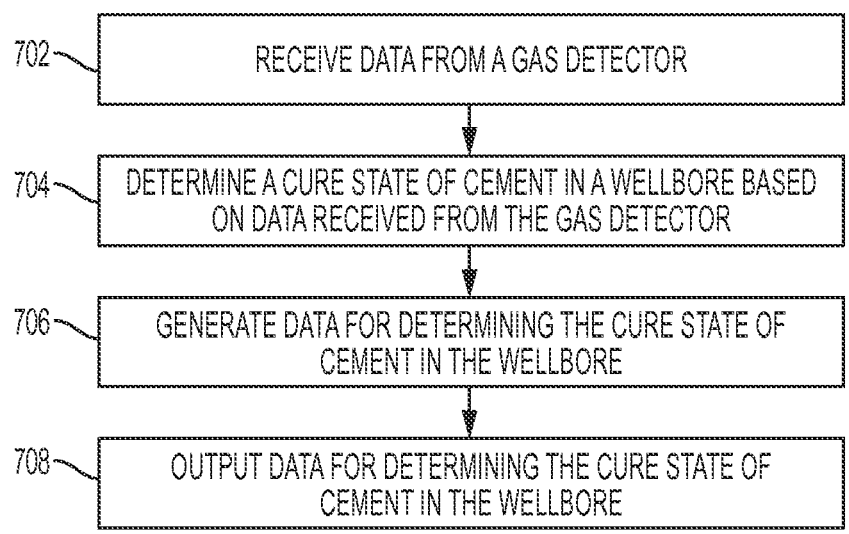
FIG. 7 is a flow chart depicting an example of a process for determining a cure state of cement in a wellbore based on an amount of gas and a type of gas.

In block 606 a cure state of cement in the wellbore is determined based on the gas detected at the surface of the wellbore. The cure state of cement in the wellbore can represent an extent of curing of cement in the wellbore (e.g., an extent of curing of the cemented interior 128 of the casing shoe 122 or an extent of curing of cement in between the casing string 106 and the wellbore 102). In some examples, the computing device can determine the cure state of cement in the wellbore based on the gas detected at the surface of the wellbore. For example, FIG. 7 is a flow chart depicting an example of a process for determining a cure state of cement in a wellbore based on an amount of gas and a type of gas.

In block 702, data is received from a gas detector. In some examples, the computing device can receive data from the gas detector device. The data can be any data transmitted from the gas detector device to the computing device (e.g., data transmitted from the gas detector device to the computing device in block 604 of FIG. 6).

In block 704, a cure state of cement in the wellbore is determined based on data received from the gas detector device. In some examples, the data can represent an amount of gas and a type of gas detected by the gas detector at a surface of the wellbore. The computing device can execute operations for determining the cure state of cement in the wellbore based on the amount of gas and the type of gas detected by the gas detector device. For example, the computing device can determine the cure state of cement in the wellbore based on a concentration of $CO_2$, $H_2$, $O_2$, or $H_2O$ in the amount of gas and the type of gas detected. The computing device can determine that cement in the wellbore is cured if the amount of gas and the type of gas detected includes a gas such as $CO_2$, $H_2$, or $O_2$. In another example, the computing device can determine that the cement in the wellbore is not cured if the amount of gas and the type of gas detected includes $H_2O$. In another example, the computing device can execute operations for determining the cure state of cement based on the amount of gas and the type of gas entering the wellbore and the amount of gas and the type of gas exiting the wellbore. For example, the computing device may execute operations for causing the computing device to apply data (e.g., data about the amount of gas and the type of gas entering the wellbore and the amount of gas and the type of gas exiting the wellbore) to a mass balance equation.

In some examples, the computing device can determine the cure state of cement in the wellbore based on data received from the gas detector device and other data. For example, the computing device can execute operations for determining the cure state of cement in the wellbore based on the amount of gas and the type of gas detected, and a type of cement in the wellbore. As an example, the computing device can determine the cure state of cement in the wellbore based on a type of cement (e.g., Portland cement) in a cemented interior of a casing shoe (e.g., the cemented interior 128 of the casing shoe 122). As water is added to the type of cement, the following cement hydration reactions can occur:

  (i)

  (ii)

  (iii)

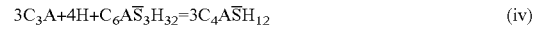  (iv)

  (v)

  (vi)

In the hydration reactions above, hydration reaction (i) is an example of a hydration reaction between tricalcium silicate ($C_3S$) in the cement and water. In hydration reaction (i) water and $C_3S$ react to yield calcium silicate hydrate ($C_3S_2H_8$) and calcium hydroxide (CH). Hydration reaction (ii) is an example of a hydration reaction between dicalcium silicate ($C_2S$) in the cement and water. Hydration reaction (iii) is an example of a hydration reaction between calcium aluminate ($C_3A$), water, and gypsum ($C\overline{S}H_2$). Hydration reaction (iii) yields mineral ettringite ($C_6A\overline{S}_3H_{32}$). Hydration reaction (iv) is an example of a hydration reaction between tricalcium aluminate ($C_3A$) in the cement, water, and ettringite. Hydration reaction (iv) yields calcium monosulfoaluminate ($C_4A\overline{S}H_{12}$). Hydration reaction (v) is an example of a hydration reaction between tricalcium aluminate in the cement, water, and calcium hydroxide. Hydration reaction (v) yields tetracalcium aluminate hydrate ($C_4AH_{13}$). Hydration reaction (vi) is an example of a hydration reaction between tetracalcium aluminoferrite ($C_4AF$), water, and calcium hydroxide, which yields calcium aluminoferrite hydrate ($C_6AFH_{12}$).

In some examples, each of the hydration reactions (i)-(vi) can occur independently and can indicate an extent of curing of the cement in the wellbore. The computing device can execute operations to determine which of the hydration reactions (i)-(vi) have occurred based on the amount of gas and the type of gas detected. The computing device can determine the extent of curing of the cement in the wellbore based on the hydration reaction (i)-(vi) that have occurred.

In other examples, the computing device can execute operations for determining the cure state of cement in the wellbore based on the amount of gas and the type of gas detected, and a type of drill device (e.g., a rock drill device or a polycrystalline diamond compact drill device) used for drilling cement in the wellbore. The computing device may also execute operations for determining the cure state of cement in the wellbore based on the amount of gas and type of gas entering and exiting the wellbore. As an example, the computing device can compare the amount of gas and the type of gas entering and exiting the wellbore. The computing device may determine the cure state of cement in the wellbore based on an increase or decrease in an amount of $CO_2$, $H_2$, $O_2$, or $H_2O$ entering and exiting the wellbore.

In block 706, data is generated for determining the cure state of cement in the wellbore. In some examples, the computing device can generate data for determining the cure state of cement in the wellbore. The data can be based on data transmitted from the gas detector device to the computing device (e.g., data transmitted from the gas detector device to the computing device in block 604 of FIG. 6). For example, the computing device can execute operations for generating data about a concentration of $CO_2$, $H_2$, $O_2$, or $H_2O$ in the amount of gas and the type of gas detected at the surface of the wellbore by the gas detector device. In another example, the computing device can execute operations for generating data about a cure state of cement in the wellbore as determined by the computing device (e.g., the cure state of cement in the wellbore determined in block 704).

In block 708, data is outputted for determining the cure state of cement in the wellbore. In some examples, the computing device can output data for determining the cure state of cement in the wellbore. The data can be based on data transmitted from the gas detector device to the computing device (e.g., data transmitted from the gas detector device to the computing device in block 604 of FIG. 6). For example, the computing device can execute one or more operations for outputting data representing an amount of gas and a type of gas detected by the gas detector device. In another example, the computing device can execute one or more operations for outputting data representing a concentration level of the amount of gas and the type of gas detected at the surface of the wellbore by the gas detector device. In another example, the computing device can execute one or more operations for outputting data representing a hydration reaction that has occurred (e.g., the hydration reactions (i)-(vi) in block 704).

Returning to FIG. 6, in block 608, the computing device can determine if the cure state of the cement in the wellbore is below a threshold. For example, the computing device can determine the extent of curing of the cement in the wellbore (e.g., at block 6060) and compare the extent of curing to a threshold extent of curing. The computing device may include a memory (e.g., the memory 508) that may include instructions for receiving data representing the threshold (e.g., from another computing device) or indicia of a user input (e.g., if the user programs the computing device to include the data). If the extent of curing of the cement in the wellbore is above the threshold, gas produced by drilling cement in the casing shoe can continue to be detected at the surface of the wellbore (e.g., at block 602).

In some examples, the process for determining a cure state of cement in a wellbore further includes, in block 610, outputting an alarm response. The computing device may output an alarm in response to determining that the cure state of cement in the wellbore is below the threshold.

In some aspects, systems and methods for determining an extent of curing of cement in the wellbore based on a type of gas and an amount of gas produced during drilling operations are provided according to one or more of the following examples:

Example #1

A method can include detecting a gas from the wellbore. The gas being produced by contact between a drill device or milling device on a downhole tool positioned in the wellbore and cement in the wellbore. The method can also include transmitting data representing an amount of gas and a type of gas detected to a computing device that determines a cure state of cement in the wellbore based on the amount of gas and the type of gas.

Example #2

The method of Example #1 may feature transmitting data representing the amount of gas and the type of gas detected including transmitting data to the computing device, the data representing a concentration level of the amount of gas and the type of gas detected.

Example #3

The method of Example #2 may feature transmitting data representing the concentration level of the amount of gas and the type of gas including transmitting data representing a concentration of carbon dioxide, hydrogen, oxygen, or water ($H_2O$) in the amount of gas and the type of gas detected.

Example #4

The method of any of Examples #1-3 may feature detecting the gas from the wellbore including detecting the amount of gas and the type of gas from the wellbore using a mass spectrometer or a purge trap device.

Example #5

The method of any of Examples #1-4 may feature detecting the gas from the wellbore including detecting an amount of gas and a type of gas entering the wellbore and an amount of gas and a type of gas exiting the wellbore.

Example #6

The method of any of Examples #1-5 may feature transmitting data representing the amount of gas and the type of gas detected to the computing device including transmitting data to the computing device that determines the cure state of cement in the wellbore based on the amount of gas and the type of gas and a type of cement in the wellbore.

Example #7

The method of any of Examples #1-6 may feature transmitting data representing the amount of gas and the type of gas detected to the computing device including transmitting data to the computing device that determines the cure state of cement in the wellbore based on the amount of gas and the type of gas and a type of the drill device or milling device.

Example #8

The method of any of Examples #1-7 may feature transmitting data representing the amount of gas and the type of gas detected to the computing device including transmitting data to the computing device that outputs an alarm in response to determining that the cure state of cement in the wellbore is below a threshold.

Example #9

The method of any of Examples #1-8 may feature transmitting data representing the amount of gas and the type of gas detected including transmitting data to the computing device for determining subsequent drilling operations based on the cure state of cement in the wellbore.

Example #10

A system can include a drilling device or a milling device coupled to a downhole tool that is positionable in a wellbore. The drilling device or milling device can be operable for drilling cement in a casing shoe coupled to a casing in the wellbore. The casing can be set within the wellbore by cement injected between the casing and the wellbore. The system can further include a gas detecting device. The gas detecting device can be positionable proximate to the wellbore for detecting a gas at a surface of the wellbore, the gas being produced by contact between the drilling device or milling device and the cement in the casing shoe. The system can further include a processing module communicatively coupled to the gas detecting device for receiving data representing an amount of gas and a type of gas detected at the surface of the wellbore for determining a cure state of cement in the wellbore.

Example #11

The system of Example #10 may feature the processing module being communicatively coupled to the gas detecting device for receiving data corresponding to a concentration level of the amount of gas and the type of gas detected at the surface of the wellbore.

Example #12

The system of any of Examples #10-11 may feature the gas detecting device being operable for detecting a concentration of carbon dioxide, hydrogen, oxygen, or water ($H_2O$) in the amount of gas and the type of gas detected at the surface of the wellbore.

Example #13

The system of any of Examples #10-12 may feature the gas detecting device including at least one of a mass spectrometer or a purge trap device.

Example #14

The system of any of Examples #10-13 may feature the processing module comprising machine-readable code for outputting an alarm in response to determining that the cure state of cement in the wellbore is below a threshold.

Example #15

A non-transitory computer-readable storage medium having program code that is executable by a processor device to cause a computing device to perform operations. The operations can include receiving data from a gas detecting device, the data representing an amount of gas and a type of gas detected at a surface of a wellbore. The amount of gas and the type of gas being produced by contact between a drilling device and cement in a casing shoe. The casing shoe being coupled to a casing in the wellbore and the casing being set within the wellbore by cement between the casing and the wellbore. The operations can also include generating data for determining a cure state of cement in the wellbore using data transmitted from the gas detecting device. The operations can further include outputting data for determining the cure state of cement in the wellbore using data transmitted from the gas detecting device.

Example #16

The storage medium of Example #15 may feature the operation of receiving data from the gas detecting device including receiving data representing a concentration level of the amount of gas and the type of gas detected at the surface of the wellbore.

Example #17

The storage medium of any of Examples #15-16 may feature the operation of generating data for determining the cure state of cement in the wellbore using data transmitted from the gas detecting device including generating data representing a concentration level of carbon dioxide, hydrogen, oxygen, or water ($H_2O$) in the amount of gas and the type of gas detected at the surface of the wellbore.

Example #18

The storage medium of Example #17 may feature the operation of determining the cure state of cement in the wellbore based on the concentration level of carbon dioxide, hydrogen, oxygen or water ($H_2O$) detected at the surface of the wellbore.

Example #19

The storage medium of any of Examples #15-18 may feature the operation of determining the cure state of cement in the wellbore based on a type of cement in the casing shoe and the amount of gas and the type of gas detected at the surface of the wellbore.

Example #20

The storage medium of any of Examples #15-19 may feature the operation of outputting data including outputting an alarm in response to determining that the cure state of cement in the wellbore is below a threshold.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:
1. A method comprising:
   detecting, by a gas detecting device positioned at a surface of and proximate to a wellbore, a gas exiting the wellbore at the surface, the gas being produced by contact between a drill device or milling device on a downhole tool positioned in the wellbore and cement in the wellbore; and transmitting data representing an amount of gas and a type of gas detected to a computing device that determines a cure state of cement in the wellbore based on the amount of gas and the type of gas.

2. The method of claim 1, wherein transmitting data representing the amount of gas and the type of gas detected includes transmitting data to the computing device, the data representing a concentration level of the amount of gas and the type of gas detected.

3. The method of claim 2, wherein transmitting data representing the concentration level of the amount of gas and the type of gas includes transmitting data representing a concentration of carbon dioxide, hydrogen, oxygen, or water ($H_2O$) in the amount of gas and the type of gas detected.

4. The method of claim 1, wherein the gas detecting device comprises a mass spectrometer or a purge trap device.

5. The method of claim 1 further comprising detecting an amount of gas and a type of gas entering the wellbore.

6. The method of claim 1, wherein transmitting data representing the amount of gas and the type of gas detected to the computing device includes transmitting data to the computing device that determines the cure state of cement in the wellbore based on the amount of gas and the type of gas and a type of cement in the wellbore.

7. The method of claim 1, wherein transmitting data representing the amount of gas and the type of gas detected to the computing device includes transmitting data to the computing device that determines the cure state of cement in the wellbore based on the amount of gas and the type of gas and a type of the drill device or milling device.

8. The method of claim 1, wherein transmitting data representing the amount of gas and the type of gas detected to the computing device includes transmitting data to the computing device that outputs an alarm in response to determining that the cure state of cement in the wellbore is below a threshold.

9. The method of claim 1, wherein transmitting data representing the amount of gas and the type of gas detected includes transmitting data to the computing device for determining subsequent drilling operations based on the cure state of cement in the wellbore.

10. A system comprising:
a drilling device or a milling device coupled to a downhole tool that is positionable in a wellbore, the drilling device or milling device being operable for drilling cement in a casing shoe coupled to a casing in the wellbore, the casing being set within the wellbore by cement injected between the casing and the wellbore;
a gas detecting device positionable at a surface of and proximate to the wellbore for detecting a gas exiting the wellbore at the surface, the gas being produced by contact between the drilling device and the cement in the casing shoe; and
a processing module communicatively coupled to the gas detecting device for receiving data representing an amount of gas and a type of gas detected at the surface of the wellbore for determining a cure state of cement in the wellbore.

11. The system of claim 10, wherein the processing module is communicatively coupled to the gas detecting device for receiving data corresponding to a concentration level of the amount of gas and the type of gas detected at the surface of the wellbore.

12. The system of claim 10, wherein the gas detecting device is operable for detecting a concentration of carbon dioxide, hydrogen, oxygen, or water ($H_2O$) in the amount of gas and the type of gas detected at the surface of the wellbore.

13. The system of claim 10, wherein the gas detecting device includes at least one of a mass spectrometer or a purge trap device.

14. The system of claim 10, wherein the processing module comprises machine-readable code for outputting an alarm in response to determining that the cure state of cement in the wellbore is below a threshold.

15. A non-transitory computer-readable storage medium having program code that is executable by a processor device to cause a computing device to perform operations, the operations comprising:
receiving data from a gas detecting device positioned at a surface of and proximate to a wellbore, the data representing an amount of gas and a type of gas detected exiting the wellbore at the surface, the amount of gas and the type of gas being produced by contact between a drilling device and cement in a casing shoe, the casing shoe being coupled to a casing in the wellbore and the casing being set within the wellbore by cement between the casing and the wellbore;
generating data for determining a cure state of cement in the wellbore using data transmitted from the gas detecting device; and
outputting data for determining the cure state of cement in the wellbore using data transmitted from the gas detecting device.

16. The non-transitory computer-readable storage medium of claim 15, wherein the operation of receiving data from the gas detecting device includes:
receiving data representing a concentration level of the amount of gas and the type of gas detected at the surface of the wellbore.

17. The non-transitory computer-readable storage medium of claim 15, wherein the operation of generating data for determining the cure state of cement in the wellbore using data transmitted from the gas detecting device includes:
generating data representing a concentration level of carbon dioxide, hydrogen, oxygen, or water ($H_2O$) in the amount of gas and the type of gas detected at the surface of the wellbore.

18. The non-transitory computer-readable storage medium of claim 17, further comprising program code to cause the computing device to perform the operation of:
determining the cure state of cement in the wellbore based on the concentration level of carbon dioxide, hydrogen, oxygen or water ($H_2O$) detected at the surface of the wellbore.

19. The non-transitory computer-readable storage medium of claim 15, further comprising program code to cause the computing device to perform the operation of:
determining the cure state of cement in the wellbore based on a type of cement in the casing shoe and the amount of gas and the type of gas detected at the surface of the wellbore.

20. The non-transitory computer-readable storage medium of claim 15, wherein the operation of outputting data includes outputting an alarm in response to determining that the cure state of cement in the wellbore is below a threshold.

* * * * *